US006156524A

United States Patent [19]
Fournier et al.

[11] Patent Number: 6,156,524
[45] Date of Patent: Dec. 5, 2000

[54] **REAGENT FOR THE DETECTION OF *STAPHYLOCOCCUS AUREUS* BY AGGLUTINATION**

[75] Inventors: Jean-Michel Fournier; Alain Boutonnier, both of Paris, France

[73] Assignee: Institut Pasteur, Paris, France

[21] Appl. No.: 08/452,786

[22] Filed: May 30, 1995

Related U.S. Application Data

[63] Continuation of application No. 08/148,409, Nov. 8, 1993, abandoned, which is a continuation of application No. 07/955,236, Oct. 5, 1992, abandoned, which is a continuation of application No. 07/415,231, Aug. 23, 1989, abandoned.

[30] Foreign Application Priority Data

Dec. 24, 1987 [FR] France ................................. 87 18166
Dec. 24, 1987 [FR] France ................................ 87 18 166
Dec. 22, 1988 [WO] WIPO ..................... PCT/FR88/00637

[51] Int. Cl.$^7$ ............................................... G01N 33/569
[52] U.S. Cl. .................... 435/7.33; 435/7.2; 435/973; 436/518; 436/523; 436/526; 436/534; 436/531; 436/828; 530/387.1; 530/387.5; 530/388.4; 530/391.1; 424/130.1; 424/137.1; 424/150.1; 424/165.1
[58] Field of Search ................................. 435/7.33, 973, 435/7.2; 436/518, 526, 531, 534, 828, 523; 530/387.1, 387.5, 388.4, 391.1; 424/130.1, 137.1, 150.1, 165.1

[56] References Cited

U.S. PATENT DOCUMENTS 5,496,706  3/1996  Kuusela et al. ......................... 435/7.33
5,776,712  7/1998  Kuusela et al. ......................... 435/7.33

OTHER PUBLICATIONS

Ruane et al., "Failure of Rapid Agglutination Methods to Detect Oxacillin–Resistant *Staphlyococcus aureus*," *Journal of Clinical Microbiology*, vol. 24, No. 3, (1986), pp. 490–492.

Fournier et al., "Predominance of Capsular Polysaccharide Type 5 among Oxacillin–Resistant *Staphylococcus aureus*," *Journal of Clinical Microbiology*, vol. 25, No. 10, (1987), pp. 1932–1933.

Nichols et al., "Agglutination and Agglutination Inhibition Assays," in Manual of Clinical Laboratory Immunology, Rose et al., eds., American Society for Microbiology, Washington, D.C., (1980), pp. 49–56.

Polysciences, Inc. 1986–1987 Catalog.

Fournier et al., "New Latex Reagent Using Monoclonal Antibodies to Capsular Polysaccharide for Reliable Identification of Both Oxacillin–Susceptible and Oxacillin–Resistant *Staphylococcus aureus*," *Journal of Clinical Microbiology*, vol. 31, No. 5, (1993), pp. 1342–1344.

Frobisher. 1968. *Fundamentals of Microbiology*, 8th Ed. p. 348.

Chemical Abstracts 125(5):52886, 1996.

Davis et al, Eds. Microbiology, 3rd Edition, Harper & Row, Publishers, Hagerstown, p. 627, 1980.

Fournier et al., "*Staphylococcus aureus* Strains Which are Not Identified by Rapid Agglutination Methods are of Capsular Serotype 5," J. Clin. Microbiol; 27(6):1372–1374, 1989.

Fournier et al., "New Latex Reagent Using Monoclonal Antibodies to Capsular Polysaccharide for Reliable Detection of Both Oxacillin . . . " J. Clin. Microbiol., 31(5):1342–44, 1993.

Jawetz et al., ed., Review of Medical Microbiology, 11th Edition; Lange Medical Publications, Los Altos, pp. 175–178, 1974.

Karakawa et al., "Method for the Serological Typing of the Capsular Polysaccharides of *Staphylococcus Aureus*," J. Clin. Microbiol. 22(3):445–447, 1985.

Speers et al., "Evaluation of Four Methods for Rapid Identification of *Staphylococcus Aureus* from Blood Cultures," J. Clin.Mmicrobiol., 36(4):1032–1034, 1998.

Ad Luijendijk et al., Comparison of Five Tests for Identification of *Staphylococcus aureus* from Clinical Samples, *J. Clinical Microbiology* (1996) 34:2267–2269, No. 9.

*Primary Examiner*—Jennifer Graser
*Attorney, Agent, or Firm*—Finnegan, Henderson, Farabow, Garrett & Dunner, L.L.P.

[57] ABSTRACT

Reagents and methods for the detection of *Staphylococcus aureus* are provided. The reagents contain an antibody that binds to a capsular polysaccharide of type 5 of *Staphylococcus aureus*, and can be used in methods for detection of oxacillin resistant *Staphylococcus aureus* that escapes detection by agglutination in the presence of fibrinogen and antibodies directed against protein A of Staphylococcus.

23 Claims, No Drawings

REAGENT FOR THE DETECTION OF *STAPHYLOCOCCUS AUREUS* BY AGGLUTINATION

This application is a continuation of application Ser. No. 08/148,409, filed Nov. 8, 1993 now abandoned, which is a continuation of application Ser. No. 07/955,236, filed Oct. 5, 1992, now abandoned, which is a continuation of application Ser. No. 07/415,231, filed Aug. 23, 1989, now abandoned which is a U.S. National stage application of International Application PCT/FR88/00637 filed on Dec. 22, 1988.

The present invention relates to a reagent for the detection of *Staphylococcus aureus* by agglutination.

Various reagents are already known for the detection of *Staphylococcus aureus*. These reagents are based on the search for either protein A of Staphylococcus or the affinity factor for fibrinogen, or both simultaneously.

Protein A is an antigen of protein nature, an external component of the wall of the majority of the strains of *Staphylococcus aureus* of human origin (85 to 95%). By a non-immunological process, protein A binds the Fc fragment of the immunoglobulins, leaving the Fab part free.

If strains of *Staphylococcus aureus* possessing protein A and sheep red blood cells or latex particles sensitized, for example, with rabbit anti-sheep red blood cells serum are placed together, an agglutination visible to the naked eye is observed within a few minutes.

The affinity factor for fibrinogen which is attached to the surface of *Staphylococcus aureus* reacts directly with fibrinogen. This affinity factor for fibrinogen can be determined within a few seconds by placing in contact the strain under study and sheep red blood cells (passive hemagglutination) or latex particles, one or other being coated with fibrinogen.

Various published studies show that a certain number of strains of *Staphylococcus aureus* are not identified by these reagents. Their percentage varies from 1 to 5% when these studies are carried out on all of the *Staphylococci aureus* isolated. But this percentage of failure is larger when only the strains resistant to oxacillin (or meticillin) are taken into consideration and this percentage attains 25% in a recent study carried out with 73 strains of *Staphylococcus aureus* resistant to oxacillin (see P. J. Ruane et al., J. Clin. Microbiol. 24, 490, 1986).

In a study carried out under the direction of one of the inventors on 183 strains of *Staphylococcus aureus* isolated from patients in 5 hospitals in Paris and the Paris region, it has been found that 7 strains (4%) are not agglutinated by any of the three reagents used (STAPHYSLIDE®, STAPHAUREX® and PASTOREX® STAPH). If only the 50 strains resistant to oxacillin are considered, it is found that 6 strains (12%) are falsely negative with the commercial reagents. Hence, these results are in agreement with those described in the literature.

Two hypotheses may be envisaged to explain the fact that some strains of *Staphylococcus aureus* are not agglutinated by the commercial reagents:

1) These strains produce protein A in an amount too small for there to be a reaction between this protein and the latex particles adequate to lead to bacterial agglutination.
2) Protein A is produced in normal amounts, but this antigen as well as the affinity factor for fibrinogen are masked by one or more other antigens and are thus inaccessible to the latex particles.

In a study carried out under the direction of one of the inventors, it has been shown that the strains non-agglutinated by the latex particles produce as much protein A as the other strains. This result thus makes it possible to eliminate the first hypothesis. It was then shown, by determining the capsular polysaccharide by means of an immunoenzymatic reaction utilizing monoclonal antibodies, that all of the strains non-agglutinated by the latex particles sensitized by fibrinogen and against protein A possess the capsular polysaccharide. Finally, the antigens exposed at the surface of the staphylococcus and, consequently, capable of reacting with the latex particles were studied by immunofluorescence. This study focused, on the one hand, on protein A (by utilizing the Fc fragment of human immunoglobulin and pepsinized F(ab')$_2$ fragments of anti-human Fc sheep immunoglobulins labelled with fluorescein) and, on the other, on the capsular polysaccharide (by utilizing mouse monoclonal antibodies of the M isotype specific for the capsular polysaccharide and F(ab')$_2$ fragments of anti-mouse M immunoglobulin goat immunoglobulins labelled with rhodamine). This study clearly showed that protein A is not exposed, or then only in very small amount at the surface of the bacteria which are not agglutinated by the latex, and that the surface of these bacteria is, on the other hand, totally masked by the capsular polysaccharide. As a control, it was verified that the strains which are agglutinated by the latex particles do indeed display protein A at their surface.

Thus, this study shows that the capsular polysaccharide synthesized by some strains of *Staphylococcus aureus* masks all of the bacterium, masks the antigens capable of being recognized by the commercial reagents and thus prevents the identification of these strains as belonging to the *Staphylococcus aureus* species by the fact of their agglutination by the commercial reagents.

The result of this study and, in particular the fact that the strains of *Staphylococcus aureus* which do not exhibit protein A at the surface are capsulated strains, the capsular polysaccharides of which mask the protein A has made it possible to design a reagent for the detection of the strains of *Staphylococcus aureus* which possesses a greater reliability than the known reagents.

A subject of the present invention is thus a reagent for the detection by agglutination of *Staphylococcus aureus* of the type comprising particles in suspension to which are bound fibrinogen and antibodies recognized by affinity by the protein A of staphylococcus, characterized in that it contains particles in suspension to which are bound at least one antibody recognizing specifically a capsular polysaccharide of *Staphylococcus aureus*.

Another subject of the present invention is a procedure for the detection by agglutination of *Staphylococcus aureus* in a sample, which consists of mixing the sample with a reagent according to the invention and of observing whether an agglutination occurs.

At present 11 typeable capsular polysaccharides have been identified by essentially immunological methods. See in this connection: W. W. Karakawa et al., Capsular polysaccharides of *Staphylococcus aureus* p. 285–293. In J. B. Robbins, J. C. Hill, and J. C. Sadoff (ed.) Seminars in infectious disease. vol. 4. Bacterial vaccines. Thieme Stratton. Inc. New York; W. W. Karakawa et al. J. Clin. Microbiol. 22:445–447, 1985; Sompolinsky et al., J. Clin. Microbiol. 22:828–834, 1985.

The purification and the biochemical and immunological characterization of the capsular polysaccharide of type 8 were carried out in 1984 (J. M. Fournier et al., Infect. Immun. 45:87–93) and those of type 5 in 1987 (J. M. Fournier et al., Ann. Inst. Pasteur/Microbiol. 138:561–567).

Specific monoclonal antibodies of the capsular polysaccharides 5 and 8 have been described (H. K. Hochkeppel et al., J. Clin. Microbiol. 25:526–530, 1987, and M. J. Nelles et al., Infect. Immun. 49:14–18, 1985).

Furthermore, epidemiological studies carried out on a large number of strains of *Staphylococcus aureus* isolated from patients have shown that 70 to 80% of these strains possess one or other of the capsular polysaccharides 5 and 8 (for example R. D. Arbeit et al., Diagn. Microbiol. Infect. Dis. 2:85–91, 1984).

Also in the present invention the antibodies recognizing a capsular polysaccharide of *Staphylococcus aureus* are advantageously constituted by at least antibodies recognizing a capsular polysaccharide of type 5 or 8 and preferably simultaneously by antibodies recognizing a capsular polysaccharide of type 5 and antibodies recognizing a capsular polysaccharide of type 8.

But it is obvious that the most reliable diagnostic reagent contains a set of antibodies recognizing the different types of capsular polysaccharides.

In the reagent according to the invention, the different antibodies and fibrinogen may be bound to only one suspension of particles or be bound to different suspensions of particles in a proportion of one or more types of component per suspension of particles) which are then mixed to constitute the reagent.

The particles in suspension used in the reagent according to the invention are in particular latex particles such as polystyrene beads or similar particles, having preferably a size less than 2 micrometers. As an example mention may be made of ESTAPOR particles marketed by the Rhône-Poulenc Company such as particles of polystyrene K 109, having a diameter of 0.8 micrometer, particles of polystyrene having carboxyl groups, PSI 480, having a diameter of 0.8 micrometer.

Magnetic gels may also be used such as gels of polyacrylamide and/or agarose containing magnetic particles which are described in FR-A-2 334 106. Gels such as ULTROGEL® and MAGNOGEL® from the IBF Company may also be used.

The antibodies used in the present invention may be animal or human antibodies, polyclonal or monoclonal.

The antibodies recognized by affinity by protein A of staphylococcus are, in particular, antibodies of the IgG class. They may be replaced by Fc fragments of these immunoglobulins.

In the case of polyclonal antibodies, a human or animal plasma, normal or immunized, containing these antibodies or antibodies purified according to standard methods may be used for the preparation of the reagent.

In the case of monoclonal antibodies, a supernatant of a hybridoma culture or ascites fluid prepared in mice, or antibodies in the purified state may be used.

In order to bind fibrinogen, a human or animal plasma, normal or hyperimmunized, or fibrinogen purified according to standard methods may be used.

The binding of these molecules to the particles in suspension, usually latex, may be accomplished in various ways:

the binding may be spontaneous during the course of incubation of the latex particles in a solution containing these molecules, for example an incubation of 30 minutes at 56° C. is often sufficient.

this binding can also be carried out by creating a covalent linkage between the antibodies and the carboxylic groups present on some of the latex particles (ESTAPOR PSI 480). It is possible to use, for example, a carbodiimide to establish the covalent linkage.

The concentration of the molecules to be bound to the latex particles, which must be determined for each molecule according to known methods, is usually lower than 200 micrograms per mg of latex. In the case of the use of molecules as components of plasma, a dilution of this plasma to $1/1000$ may be used.

The following examples illustrate the present invention.

EXAMPLE 1 a) Preparation of latex particles sensitized with fibrinogen and antibodies contained in human plasma, including IgG.

A suspension of latex (ESTAPOR, K 109) is brought to a concentration of 2% in glycine (0.27 M)—sodium chloride (0.15 M)—sodium azide (0.04 g/liter) buffer, called CGA, pH 8. A volume of this suspension is mixed with an equal volume of human plasma diluted $1/1000$ in the same buffer, then incubated for 30 minutes at 56° C. with shaking. After washing, the sensitized latex particles are resuspended in a CGA buffer containing 0.05% of human plasma.

b) Preparation of latex particles sensitized with purified monoclonal antibodies recognizing the capsular polysaccharide of type 8.

A suspension of latex (ESTAPOR, ref. K. 109) is brought to a concentration of 2% in glycine (0.17 M)—sodium chloride (0.15 M)—sodium azide (0.04 g/liter) buffer, called CGA, pH 9.2. A volume of this suspension is mixed with an equal volume of purified antibodies dissolved in the same buffer. The final concentration of antibodies is 100 micrograms of antibodies per mg of latex. After incubation for 30 minutes at 37° C., the sensitized latex particles are washed, then resuspended in the CGA buffer containing 0.1% of bovine serum albumin.

c) Preparation of the reagent.

The suspension obtained in a and the suspension obtained in b are mixed in equal proportions to constitute the reagent.

EXAMPLE 2

One works as in example 1 but by using in step b a mixture of monoclonal antibodies recognizing specifically the polysaccharides of types 8 and 5.

For this purpose a suspension of Estapor latex (ref. K 109) at a concentration of 4% in 0.15 M/liter glycine, 0.15 M/liter NaCl buffer, pH 8.2 (GN) is mixed to a volume of GN buffer containing a mixture of anti-type 5 and anti-type 8 monoclonal antibody in equal proportions at a final concentration of 1 mg/ml. This mixture is incubated for ½ hour at 37° C. with shaking.

A volume of this sensitized latex is mixed with GN buffer containing 3 mg/ml of bovine albumin and 0.04 g/l of sodium azide. This mixture is incubated for ½ hour at 37° C. 1 volume of this anti-type 5 and 8 latex is mixed with 1 volume of latex particles sensitized with fibrinogen and antibodies of human plasma.

EXAMPLE 3

One works as in example 1 but by using in step b a mixture of 11 antibodies recognizing specifically the 11 known capsular polysaccharides of *Staphylococcus aureus*.

EXAMPLE 4

In a study carried out under the direction of one of the inventors, the agglutinating power of a reagent prepared according to the procedure described in example 2 was compared with that of a commercial reagent (Pastorex$^R$Staph). This comparison was carried out with 183 strains of *Staphylococcus aureus* isolated from patients.

Whereas the commercial reagent only agglutinates 176 of the 183 strains, the reagent prepared according to example 2 agglutinates the 183 strains. Furthermore, the rapidity and intensity of the agglutination of the strains which were already agglutinated by the commercial reagent are very markedly improved by the utilization of the reagent prepared according to example 2.

The reagents according to the invention may be used for a rapid identification of the *Staphylococcus aureus* species by agglutination:

before isolation of the bacterium: in a biological fluid (secretion, suppuration, etc . . . ), in a culture medium (blood culture, etc . . . ), after isolation of the bacterium.

The reagents according to the invention make it possible to recognize all of the strains of *Staphylococcus aureus* which are not recognized by existing agglutinating reagents presently on the market and among which the strains resistant to oxacillin predominate. They thus possess major importance—in view of the problems which these strains, which are also most often multiresistant, pose.

What is claimed is:

1. A reagent for the detection by agglutination of *Staphylococcus aureus*, comprising a mixture of (A) particles in suspension to which are bound fibrinogen and antibodies, which have affinity for protein A of Staphylococcus, and (B) particles in suspension to which are bound at least one antibody, which binds to a capsular polysaccharide of type 5 of *Staphylococcus aureus*, wherein said reagent can detect oxacillin resistant *Staphylococcus aureus* that is not detected by said reagent in the absence of the antibody that binds to the capsular polysaccharide.

2. The reagent according to claim 1, wherein the antibodies which bind to the capsular polysaccharide of *Staphylococcus aureus* are comprised of a mixture of antibodies which bind to the capsular polysaccharide of type 5 and antibodies which bind to a capsular polysaccharide of type 8.

3. The reagent according to claim 1, wherein the antibodies which bind to the capsular polysaccharide of *Staphylococcus aureus*, comprise a set of antibodies which bind to all typeable capsular polysaccharides.

4. The reagent according to claim 1, wherein the particles in suspension are latex particles.

5. The reagent according to claim 2, wherein the particles in suspension are latex particles.

6. The reagent according to claim 3, wherein the particles in suspension are latex particles.

7. The reagent according to claim 1, wherein the particles have a size less than 2 micrometers.

8. The reagent according to claim 2, wherein the particles have a size less than 2 micrometers.

9. The reagent according to claim 3, wherein the particles have a size less than 2 micrometers.

10. The reagent according to claim 4, wherein the particles have a size less than 2 micrometers.

11. The reagent according to claim 1, wherein the particles in suspension are magnetic gels.

12. The reagent according to claim 2, wherein the particles in suspension are magnetic gels.

13. The reagent according to claim 3, wherein the particles in suspension are magnetic gels.

14. A reagent for the detection by agglutination of *Staphylococcus aureus* comprising a mixture of (A) particles in suspension to which are bound antibodies of the IgG class, which have affinity for protein A of Staphylococcus, and fibrinogen, and (B) particles in suspension to which are bound at least one monoclonal antibody which binds to a capsular polysaccharide of type 5 of *Staphylococcus aureus*.

15. A reagent for the detection by agglutination of *Staphylococcus aureus*, wherein the reagent comprises particles in suspension to which are bound:

(A) fibrinogen;

(B) antibodies that have affinity for protein A of Staphylococcus; and (C) at least one antibody, which binds to a capsular polysaccharide of type 5 of *Staphylococcus aureus*, for the detection of oxacillin resistant *Staphylococcus aureus* that is not detected by said reagent in the absence of the antibody that binds to the capsular polysaccharide, wherein said reagent can detect oxacillin resistant *Staphylococcus aureus* that is not detected by said reagent in the absence of the antibody that binds to the capsular polysaccharide.

16. A method for the detection of *Staphylococcus aureus* comprising oxacillin resistant *Staphylococcus aureus* that escapes detection by agglutination in the presence of fibrinogen and antibodies directed against protein A of Staphylococcus in a sample by agglutination, comprising the steps of:

(a) mixing the sample with a reagent for the detection by agglutination of *Staphylococcus aureus*, comprising particles in suspension to which are bound fibrinogen and antibodies, which have affinity for protein A of Staphylococcus, further comprising particles in suspension to which are bound at least one antibody, which binds to a capsular polysaccharide of type 5 of *Staphylococcus aureus*, wherein said reagent can agglutinate oxacillin resistant *Staphylococcus aureus* that escapes detection by agglutination in the presence of only fibrinogen and antibodies directed against protein A of Staphylococcus, and (b) detecting *Staphylococcus aureus* including oxacillin resistant *Staphylococcus aureus* that escapes detection by agglutination in the presence of fibrinogen and antibodies directed against protein A of Staphylococcus by detecting agglutination in said mixture.

17. The method of claim 16, wherein the antibodies, which bind to the capsular polysaccharide of *Staphylococcus aureus*, are comprised of a mixture of antibodies that bind to a capsular polysaccharide of type 5 and antibodies that bind to a capsular polysaccharide of type 8.

18. The method of claim 16, wherein the antibodies, which bind to a capsular polysaccharide of *Staphylococcus aureus*, comprise a set of antibodies that bind to all typeable capsular polysaccharides.

19. The method of claim 16, wherein the particles in suspension are latex particles.

20. The method of claim 16, wherein the particles have a size less than 2 micrometers.

21. The method of claim 16, wherein the particles in suspension are magnetic gels.

22. The method according to claim 16, wherein the sample is a sample of blood culture.

23. A method for the detection of *Staphylococcus aureus* in a sample by agglutination, wherein the method comprises:

(I) mixing the sample with a reagent for the detection by agglutination of *Staphylococcus aureus*, wherein the reagent comprises particles in suspension to which are bound:

(A) fibrinogen;

(B) antibodies that have affinity for protein A of Staphylococcus; and (C) at least one antibody, which binds to a capsular polysaccharide of type 5 of *Staphylococcus aureus*, for agglutinating said oxacillin resistant *Staphylococcus aureus* that is not detected by said reagent in the absence of the antibody that binds to the capsular polysaccharide, wherein said reagent can detect oxacillin resistant *Staphylococcus aureus* that escapes detection by agglutination in the presence of only fibrinogen and antibodies directed against protein A of Staphylococcus, and (II) detecting *Staphylococcus aureus* including oxacillin resistant *Staphylococcus aureus* that escapes detection by agglutination in the presence of fibrinogen and antibodies directed against protein A of Staphylococcus by detecting agglutination in said mixture.

* * * * *